United States Patent [19]

Petersen

[11] 4,136,858

[45] Jan. 30, 1979

[54] SURGICAL KNEE HOLDER

[75] Inventor: Thomas D. Petersen, La Mesa, Calif.

[73] Assignee: Alvarado Orthopedic Research, Inc., La Mesa, Calif.

[21] Appl. No.: 881,356

[22] Filed: Feb. 27, 1978

[51] Int. Cl.[2] .................................................. A61F 5/04

[52] U.S. Cl. ...................................................... 269/328

[58] Field of Search ............... 269/328, 203; 5/327 R; 297/439

[56] References Cited

U.S. PATENT DOCUMENTS

| | | | |
|---|---|---|---|
| 1,852,586 | 4/1932 | McKnight | 269/203 X |
| 2,581,110 | 1/1952 | Kenworthy | 5/327 R |
| 3,880,417 | 4/1975 | Burris et al. | 5/327 R |

*Primary Examiner*—Robert C. Watson

*Attorney, Agent, or Firm*—Brown & Martin

[57] ABSTRACT

A knee holder for holding a knee into selected positions for surgery includes a base plate for mounting on an operating table, the base plate including a plurality of connecting elements extending along the length of the base plate and a leg brace for strapping to the lower leg of a patient, with pins on the leg brace for engaging selective ones of the connecting elements on the base plate for adjusting the degree of bend in the leg for operation.

8 Claims, 2 Drawing Figures

SURGICAL KNEE HOLDER

BACKGROUND OF THE INVENTION

The present invention relates to surgical devices and pertains particularly to a holder for holding the knee of a patient into selected optimum positions for knee surgery.

A considerable amount of surgery is performed for the purpose of correcting and repairing knee injuries and the like. It is important during such surgery for the knee to be positioned for optimum access to the injured portion of the knee. In the usual arrangement for knee surgery, the patient is placed on his back on an operating table with the knee bent upward above the operating table and held into position by some form of leg bracket attached to the operating table. It is desirable that the surgeon be able to adjust the knee to various selected positions and to retain the knee in the selected position. The prior art devices, while effective in holding the knee in the selected position, is normally cumbersome and does not have provision for quick and ready adjustment of the position of the knee.

It is also desirable that the leg be releasable from the leg holder for straightening the leg or knee during the operation.

It is also desirable that a knee holder be readily and easily sterilized and maintained in a sterile condition.

SUMMARY AND OBJECTS OF THE INVENTION

It is the primary object of the present invention to overcome the above problems of the prior art.

Another object of the present invention is to provide an improved knee holder for holding the knee of a patient in a desired position for surgery.

A further object of the present invention is to provide an improved knee holder that provides for quick and easy adjustment of the position of the knee of a patient.

In accordance with the primary aspect of the present invention, an adjustable knee holder comprises a base plate having adjustable connecting means thereon and a leg brace with connecting means for connecting to the leg and for selectively connecting to selected positions on the base plate.

BRIEF DESCRIPTION OF THE DRAWING

The above and other objects and advantages of the present invention will become apparent from the following description when read in conjunction with the drawings, wherein.

DETAILED DESCRIPTION OF A PREFERRED EMBODIMENT

Figure 1:
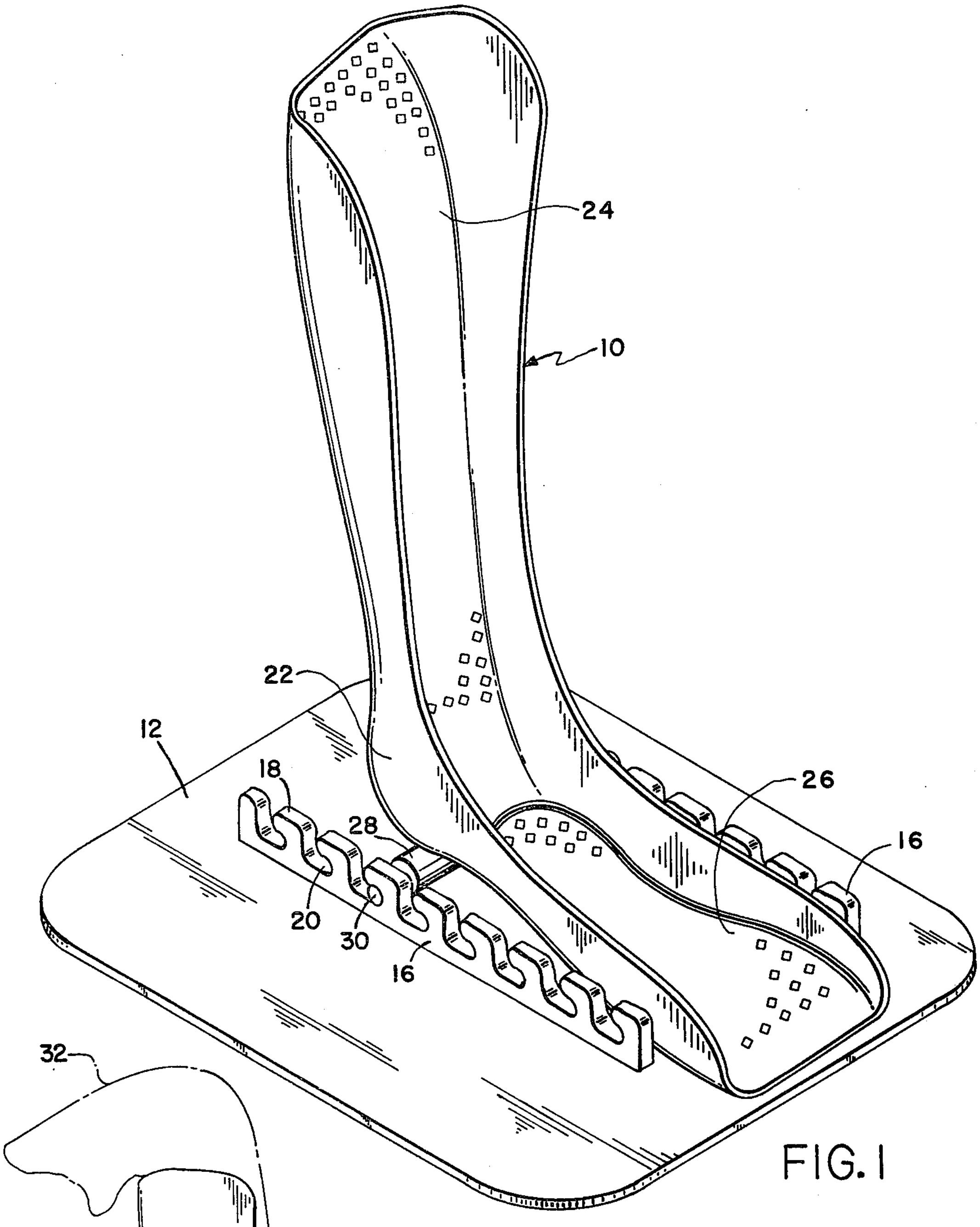
FIG. 1 is a perspective view of a knee holder in accordance with the invention.

Turning to FIG. 1 of the drawing, a knee holder in accordance with the invention is illustrated, and designated generally by the numeral 10. This knee holder comprises a generally rectangular flat base plate 12 constructed of a suitable durable material having the required strength and durability and being capable of being sterilized. The base plate, for example, may be constructed of stainless steel or the like and includes elongated connecting means on the upper surface thereof comprising spaced apart members forming first and second rows of slotted hooks 14 and 16 respectively. These rows of hooks generally extend parallel with the hook portion defined by a plurality of generally vertically extending L-shaped members having the leg portion thereof extending backward and defining a plurality of generally L-shaped slots therebetween. Each row, for example, comprises a generally L-shaped hook 18 defining in conjunction with an adjacent hook, a generally L-shaped slot 20. These generally L-shaped hooks 18 extend upward from the base plate and for a sufficient length along the base plate to provide adequate selective adjustment in the bend of a knee on which operation is to take place.

In conjunction with the base plate, a foot or lower leg bracket 22 is provided. This leg bracket comprises a generally vertically extending channel shaped leg connecting portion 24 and a generally outwardly extending channel shaped foot connecting portion 26. The foot and lower leg of a patient is placed in the channels and fastened in by a suitable strap or the like, not shown. This channel construction permits high strength light weight construction and easy connection to the foot.

The leg bracket 22 is likewise constructed of a material having the desired strength and durability and being capable of being sterilized. The leg bracket includes a connecting means for connecting to the base plate comprising a generally cylindrical bracket member 28 having hook or slot engaging pins at each end thereof, only one of which is shown at 30. These pins engage into the slots 20 beneath the hook portions of the hook 18 and are pivotal therein. This engagement between the pins and the hooks provide lateral stability of the holder as well as quick and convenient detachment of the leg brace thereof from the base plate 12. Thus, the leg holder can be selectively engaged in any one of selected ones of pairs of spaced apart hook members extending along the length of the base plate 12.

Figure 2:
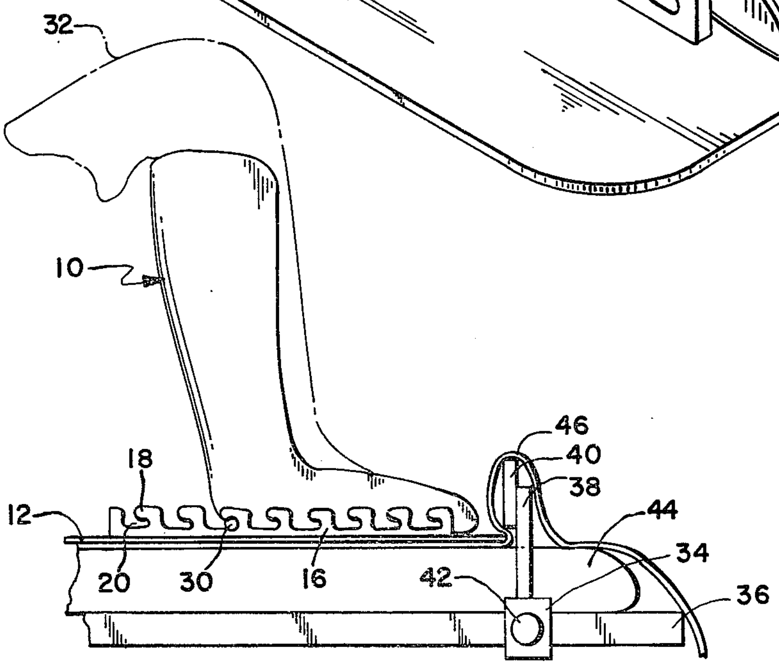
FIG. 2 is a side elevational view showing the knee holder mounted on an operating table.

As best seen in FIG. 2, this construction permits the degree of bend in a knee 32 of a patient to be adjusted. This adjustment permits more ready access to the knee. This also permits the leg to be quickly detached from the base plate and straightened if desired or when necessary.

Turning specifically to FIG. 2, there is illustrated an anchoring bracket or device for the base plate which comprises, for example, a clamp member 34 for clamping to a frame member 36 of the operating table and includes an upwardly extending arm 38 connected to a transversely extending arm or fence member 40. This bracket is connectable to the frame 36 of the operating table with an adjusting or clamping screw 42 permitting adjustment of the clamp along the length of the frame member 36. The arm 38 extends upward above the table pad 44 with the fence member 40 extending transverse above the pad 44 and beneath a sheet 46 on the operating table. This arrangement permits the bracket 10 to be kept in a sterile environment and to be anchored without disturbing the sterile environment. The sheet 46 shown in cross section, covers the entire operating table and the anchoring bracket so that they are separated from the sterile environment of the operating table. The base plate 12 and leg bracket 22 can then be sterilized and placed on top of the operating table cover 46 without danger of contamination from other portions of the operating table.

While the present invention has been illustrated and described by means of a specific embodiment, it is to be understood that numerous changes and modifications may be made in the invention without departing from the spirit and scope of the invention as defined in the appended claims.

Having described my invention, I now claim:

1. A knee holder for positioning the knee of an individual into position for surgery, said holder comprising in combination:

a base plate for securing in a fixed position on an operating table, said plate having a generally flat bottom and a generally flat top and multiple connecting means on the top thereof, and a bracket including a leg brace means for receiving and connecting to the lower leg and the foot of a patient, said bracket including pivotal connecting means having a single pivot axis for selectively engaging and pivotally connecting said bracket to said first connecting means for pivotal movement about said single pivot axis and for relative adjustment of the bracket along the base plate for supporting a leg in selected bent positions.

2. The knee holder of claim 1, wherein said first connecting means comprises means defining a plurality of individual slots extending in a row along the top of said plate, hook means defining said slots, and said slots are generally hook shaped.

3. The knee holder of claim 1, wherein said first connecting means comprises a pair of spaced apart elongated members extending generally parallel across the top of said plate, said spaced apart elongated members are shaped to define a plurality of generally L-shaped hooks and slots.

4. The knee holder of claim 1, wherein said second connecting means comprises pin means for engaging said slots.

5. The knee holder of claim 3, wherein said second connecting means comprises a pin extending outward from each side of said bracket for selective engagement with said slots.

6. The knee holder of claim 3, further comprising an anchoring bracket for securing said plate in place on an operating table, said anchoring bracket including adjustable clamping means for clamping to a table frame and including a fence member extending upward from the surface of an operating table for engagement by said plate.

7. The knee holder of claim 5, wherein said bracket is a generally L-shaped channel having a generally upwardly extending channel portion for receiving a lower leg and a generally outwardly extending portion for receiving a foot.

8. The knee holder of claim 7, wherein said foot bracket has a heel portion and said pin is secured to and extends outward from said heel portion.

* * * * *